United States Patent [19]

Giaever

[11] 3,960,488
[45] June 1, 1976

[54] METHOD AND APPARATUS FOR QUANTITATIVE SURFACE INHIBITION TEST

[75] Inventor: Ivar Giaever, Schenectady, N.Y.
[73] Assignee: General Electric Company, Schenectady, N.Y.
[22] Filed: Apr. 1, 1974
[21] Appl. No.: 457,091

[52] U.S. Cl. .......................... 23/230 B; 23/253 R; 23/253 TP; 23/259; 195/103.5 R; 195/127; 424/12
[51] Int. Cl.² .................................. G01N 33/16
[58] Field of Search ............. 23/230 B, 253 R, 259; 424/12; 195/103.5 R, 127

[56] References Cited
UNITED STATES PATENTS

| | | | |
|---|---|---|---|
| 3,645,687 | 2/1972 | Nerenberg | 23/230 B X |
| 3,674,438 | 7/1972 | Shen | 23/230 B X |
| 3,692,486 | 9/1972 | Glenn | 23/253 R X |
| 3,692,491 | 9/1972 | Trentelman | 23/230 B X |
| 3,709,661 | 1/1973 | Hubscher | 23/253 R |
| 3,718,436 | 2/1973 | Ushakoff | 23/253 R |
| 3,725,004 | 4/1973 | Johnson | 23/230 B |
| 3,736,100 | 5/1973 | Rains | 23/230 B X |
| 3,770,380 | 11/1973 | Smith | 23/230 B |
| 3,843,450 | 10/1974 | Saxholm | 23/230 B X |
| 3,853,467 | 12/1974 | Giaever | 23/230 B |

OTHER PUBLICATIONS
E. A. Kabat, "Structural Concepts in Immunology," 45, Holt, Rinehart and Winston, New York, 1968.
S. D. Elek, Brit., J. Exptl. Pathol., 30, 484 (1949).

*Primary Examiner*—Morris O. Wolk
*Assistant Examiner*—Sidney Marantz
*Attorney, Agent, or Firm*—Leo I. MaLossi; Joseph T. Cohen; Jerome C. Squillaro

[57] ABSTRACT

A metallized slide has adsorbed thereon a first monomolecular layer of particular first immunologically reactive biological particles and is covered with a suitable moisture holding medium. A test solution is then applied along a first edge of the slide, a solution containing second immunologically reactive biological particles specific to the first particles is applied along an edge perpendicular to the first edge, or midway along the slide, and the biological particles in the two solutions diffuse toward each other. The slope or distance from the first edge of a precipitation line formed on the metallized slide at the intersection of the diffused first and second biological particles is related to the concentration of the first particles in the test solution.

40 Claims, 14 Drawing Figures

METHOD AND APPARATUS FOR QUANTITATIVE SURFACE INHIBITION TEST

My invention relates to a method and apparatus for determining the concentration of immunologically reactive biological particles in a solution, and in particular, for obtaining the determination as a result of an antigen-antibody reaction inhibition test on a solid substrate surface with the unaided eye.

This application is related to my concurrently filed applications Ser. No. 457,092 entitled "Method and Apparatus for Determination of Concentration of Immunologically Reactive Biological Particles", Ser. No. 457,094 entitled "Method and Apparatus for Detecting Immunologically Reactive Biological Particles", and Ser. No. 457,093 entitled "Method and Apparatus for Detecting Immunologic Reactions by Diffusion in Gel" as well as to my copending applications Ser. No. 266,278 entitled "Method and Apparatus for Detection and Purification of Proteins and Antibodies" filed June 26, 1972, now abandoned; Ser. No. 384,113 entitled "Improved Method and Apparatus for Detection and Purification of Proteins and Antibodies" filed July 30, 1973, now abandoned, and Ser. No. 445,204 entitled "Improved Substrate for Immunological Tests and Method of Fabrication Thereof" filed Feb. 25, 1974, and assigned as herein.

Immunological reactions are highly specific biochemical reactions in which a first immunologically reactive biological particle (generally a protein) known as the antigen, combines (links) with a second protein specific to the antigen, and known as the antibody, to form an immunologically complexed protein. Immunological reactions taking place within a biological system, such as an animal or human being, are vital in combatting disease. In a biological system, the entry of a foreign protein, i.e., the antigen, causes the biological system to produce the specific antibody proteins to the antigen in a process not fully understood at this time. The antibody protein molecules have available chemical combining or binding sites which complement those of the antigen molecule so that the antigen and antibody link or bond to form an immunologically complexed protein.

Most antigens are proteins or contain proteins as an essential part, whereas all antibodies are proteins. Proteins are large molecules of high molecular weight, i.e., are polymers consisting of chains of variable numbers of amino acids. The above-cited copending applications disclose that an arbitrary protein will adhere to a substrate in a monomolecular layer only, and that no other arbitrary protein will adhere to the protein layer. On the other hand, the specifically reacting protein to the first protein adsorbed onto the substrate will immunologically bond thereto. In accordance with the teachings of those applications, this discovery is exploited to provide medical diagnostic apparatus in which a slide having a monomolecular layer of one protein adsorbed thereon is used to test suspected solutions for the presence of the specifically reacting protein thereto. If the specifically reacting protein is present in the solution, the slide after exposure to the solution has a bimolecular protein layer thereon. If the specifically reacting protein be absent from the solution, the slide after exposure to the solution has only the original monomolecular layer thereon. Optical, electrical, and chemical means for distinguishing between bimolecular and monomolecular biological particle layers are taught in the related copending applications and have different degrees of sensitivity and economy.

Because antibodies are produced by biological systems in response to invasions thereof by foregin proteins, the detection of antibodies in a biological system is of medical diagnostic value in determining the antigens to which the system has been exposed. A typical example of diagnostic detection of antibodies is the detection of antibodies to syphilis or gonorrhea in human serum. Conversely, the detection of certain antigens in a biological system also has medical diagnostic value; examples of diagnostic detection of antigens include detection of HCG-protein molecules in urine as a test for pregnancy, and detection of hepatitis-associated-antigen (HAA) molecules in the blood of prospective blood donors.

In order to perform such diagnostic test, the appropriate protein of the immunologically reacting pair must be obtained. The only known source of an antibody protein is a living biological system. More particularly, only vertebrates are known at this time to exhibit immunological reactions to the introduction of a foregin protein. For example, many antibodies are found in the blood serum of animals and human beings which have been exposed to the corresponding antigens. Many antigens, however, may be controllably produced in laboratory cultures. However, some antigens, for example, hepatitis-associated-antigens, are at present, like antibodies, only obtainable from the higher living biological systems.

It is known in the immunological art that antibody molecules functions as antigens when introduced into the system of a vertebrate to whom they are foreign proteins. Accordingly, specifically reacting antibodies to a given antibody may be readily produced in such vertebrate system.

Although the substrates (slides) described in my hereinabove-referenced patent applications are satisfactory in their performance for detecting a bimolecular layer of immunologically reactive biological particles, such slides do not by themselves indicate the concentration in a solution of the biological particles forming the second monomolecular layer on the substrate unless a timing process is used.

Another type of metallized slide known in the prior art is the anodized tantalum slide described in the articles "Interactions Among Human Blood Proteins at Interfaces", authors L. Vroman et al, Federation Proceedings, Volume 30, No. 5 (September–October, 1971) pages 1494–1502 and "Three Simple Ways to Detect Antibody-Antigen Complex on Flat Surfaces", authors A. L. Adams et al., Journal of Immunological Methods 3 (1973) pages 277–232, however, this anodized tantalum slide is less sensitive than my indium-gold alloy indium oxide slide disclosed and claimed in my above-referenced copending applications Ser. No. 445,204, especially in the detection of hepatitis. Another article related to prior art metallized slides is "Immunologic and Enzymatic Reactions Carried Out at a Solid-Liquid Interface", by Alexandre Rothen, Physiological Chemistry and Physics 5 (1973) pages 243–258.

Double diffusion immunological experiments have been carried out in the prior art on cellulose acetate membranes and in gels in which specimens containing antigens and their antibodies are applied to different areas of the wet membrane (or wells in the gel) and diffuse toward each other to form a complexed protein precipitate line. However, in such prior art experiments, the sensitivity of the test is not as high as might often be desired, and the precipitate line is generally not visible to the unaided eye until the cellulose acetate membrane or gel is suitably stained with a protein material such as Amido Black as described in the book "Method in Immunology and Immunochemistry", Vol. III, edited by C. A. Williams and M. W. Chase, Academic Press, pages 153 and 169. This staining process adds another step in the method for detecting such biological particles. Further, since the precipitate is formed in the gel, it forms only a temporary record of the immunologic reaction unless a complicated staining, washing, and drying process is employed, and the gel is subject to undesired bacteria growth. Finally, such prior art double diffusion experiments do not provide a simple method and apparatus for determining the concentration of particular immunologically reactive biological particles in a specimen such as a blood sample.

Therefore, a principal object of my invention is to provide a simple method and apparatus for determining the concentration of immunologically reactive biological particles in a solution suspected of containing such particles.

Another object of my invention is to provide a simple method and apparatus for determining by direct visual observation the concentration of immunologically reactive biological particles which are involved in an immunological reaction occurring at a solid surface.

A further object of my invention is to provide an improved method and apparatus for determining the concentration of the biological particles by a double diffusion utilizing a cellulose membrane as the diffusing medium.

A still further object of my invention is to provide an improved simple method and apparatus for determining the concentration of the biological particles by a double diffusion utilizing a gel as the diffusing medium.

Another object of my invention is to provide a simple method and apparatus for determining the concentration without the need for staining the diffusing medium, and for obtaining a durable record thereof.

A still further object of my invention is to provide a simple method and apparatus for determining the concentration of the biological particles by observing a precipitate line formed by an immunological reaction between biological particles which is visible to the unaided eye with a good contrast which is significantly better than that obtained with prior art techniques.

Briefly, and in accordance with the objects of my invention, I provide a method and apparatus for determining the concentration of first immunologically reactive biological particles in a test solution by a direct visual observation of the slope of a complexed protein precipitate line formed on a metallized solid substrate. The metallized solid substrate initially has a monomolecular layer of the first biological particles adsorbed thereon. The monomolecular layer coated metallized substrate is then covered with a moisture holding medium such as a very thin layer of gel or moistened cellulose membrane in the first two embodiments of my invention. A test solution is then applied on the moisture holding medium along one edge of the metallized substrate and a second solution containing second immunologically reactive biological particles specific to the first particles is applied along an edge perpendicular to the first edge. The test solution and second solution diffuse toward each other through the moisture holding medium and at their intersection the second biological particles will not be able to diffuse further due to being precipitated by the test solution first biological particles. The slope of the resultant precipitate line is related to the concentration of the first particles in the test solution. In another embodiment of my invention, the concentration of a plurality of different immunologically reactive biological particles, such as various components in human blood plasma, can be determined by adsorbing individual monomolecular layer strips of such components on a metallized surface of the substrate and covering such strips with a moisture holding (diffusing) medium. A solution to be tested for the various components is deposited on the diffusing medium along one edge of the substrate, a control solution containing normal concentrations of the components is deposited along the opposite edge and a solution containing immunologically reactive biological particles specific to the various components is deposited along the center line of the substrate midway between the two edges so that the three solutions are deposited parallel to each other and perpendicular to the adsorbed monolayer strips. During diffusion of the three solutions through the moisture holding medium, monolayers of the specific biological particles are formed by immunological reaction along the adsorbed monolayer strips outwardly from the center line so that the lengths of the various double layers of biological particles are related to the concentrations of the various components. A comparison of the test solution concentration of each particular component with the concentration in the control solution is obtained by visually comparing the lengths of the double layer along each component strip from the center line thereof thereby quickly determining whether the concentration of each component in the test solution is normal or abnormal. The complexed protein precipitate lines formed on the metallized surface of the solid substrate as a result of the immunological reactions for all embodiments of my invention are clearly visible with good contrast to the unaided eye without requiring the use of a staining material and form a durable record of the immunologic reactions. The precipitate line in the first two embodiments and various precipitate lines in the other embodiments are visible, as noted above, when formed with a substantially lesser amount of the biological particles than is necessary in the prior art techniques so that my method and apparatus are substantially more sensitive.

The features of my invention which I desire to protect herein are pointed out with particularity in the appended claims. The invention itself, however, both as to its organization and method of operation together with further objects and advantages thereof may best be understood by reference to the following description taken in connection with the accompanying drawings wherein:

substrate

Figure 1A:
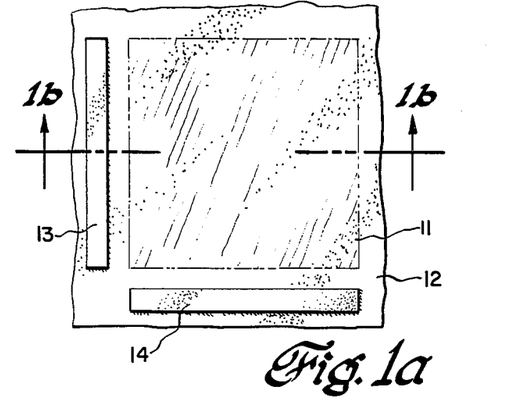
FIG. 1a is a plan view of a first embodiment of my invention utilizing a moistened cellulose membrane as a diffusing medium for two specimens.
Figure 1B:
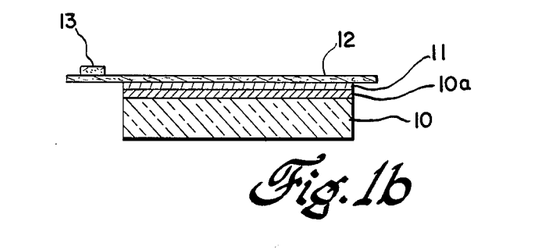
FIG. 1b is an elevation view, in section, of the apparatus illustrated in FIG. 1a taken along line 1b—1b.

Referring now to FIGS. 1a and 1b, there are shown, respectively, a plan and elevation view of a first embodiment of an apparatus, in accordance with my invention, for determining the concentration of particular immunologically reactive biological particles in a test solution by means of an indirect test performed on a solid surface, and in particular, on the surface of a metallized solid substrate. The apparatus consists of a metallized substrate 10 having adsorbed along substantially the entire metallized surface thereof a monomolecular layer 11 of the (first) biological particles being investigated, and a liquid diffusing member 12 in contact with the monomolecular layer 11 wherein the diffusing member is utilized for depositing a test solution as well as a second solution containing (second) immunologically reactive biological particles specific to the first particles.

Substrate 10 has a substantially flat top surface and is fabricated of a suitable material which may be a metal, glass, plastic or similar material. Substrate 10 is preferably in the form of a glass slide such as a conventional microscope cover glass that is readily commerically available. The top flat surface of substrate 10 is metallized in accordance with the teachings disclosed in my above-identified patent applications which are hereby incorporated by reference herein. As examples of such teachings, the metallization 10a may consist of (1) a non-continuous layer, i.e., metal particles or globules with indium being a typical metal, or (2) a first layer of the indium globules overlayed with a thin gold film, or (3) a layer of the indium globules (or a constant thickness continuous layer of indium) and a thin film of gold which is alloyed with the indium, and a thin oxide film of the indium forming the outermost surface, or (4) a metal such as nickel and oxide film thereof. The non-continuous layer of indium particles is a preferred embodiment in most applications, particularly where the size (molecular weight) of the two particular biological particles involved are similar. In cases wherein one of the particles is substantially larger than the other, such as in hepatitis wherein the hepatitis-associated antigen is substantially larger than its antibody, the third metallization has provided the most sensitive substrate. The particular metallization that is selected is therefore dependent primarily on the biological particle being investigated and such selected metallized solid substrate provides significant contrast, visible to the unaided eye, between single and double monomolecular layers of immunologically reactive biological particles and a complexed protein precipitate line formed thereof. Following the teachings in the above-referenced patent applications, substrate 10 is formed of a light-transmissive material such as glass or plastic and the indium particles evaporated on the surface of the light-transmissive substrate have diameters on the order of 1000 Angstrom although the precise size of the globules is not critical as long as they have diameters equal to a large fraction of a wavelength of visible light. The color of the indium particle metallization is a light brown. In the case of the indium-gold alloy, indium oxide film metallization, the thickness of the indium is approximately twice the thickness of the gold when initially deposited, the indium thickness being approximately 2000 A, gold is approximately 1000 A and the indium oxide film is several hundred Angstrom to obtain a bronze color of such film. In the latter metallization, the degree of oxidation of the indium determines the color of the oxidized film so that various degrees of oxidation produce different colored slides having different sensitivities for different thicknesses of the layers of the biological particles.

In the case of the metallized coating 10a on the top surface of substrate 10 being formed of particles or globules of a first metal such as indium, and also in the case of the indium globule-gold alloy and indium oxide film metallization, the top surface of such metallized coating is slightly irregular. Alternatively, such metallized coating 10a may be formed of a continuous, constant thickness layer of one or more metals and has a top surface that is substantially flat. Either type of metallized surface (slightly irregular or flat) may be utilized in my invention. Substrate 10 may be as small as a half inch square. Further details of the substrate metallization and fabrication thereof are disclosed in my above-referenced copending patent applications which are hereby incorporated by reference herein.

After selection of the appropriate metallized substrate, as determined by the particular biological particles involved in the tests to be conducted, monomolecular layer 11 of first immunologically reactive biological particles is adsorbed along substantially the entire metallized surface of the substrate. These first biological particles are the particular particles in a test solution whose concentration will be subsequently determined. The adsorption of the first biological particles may be accomplished by immersing the substrate into a solution of the particles for a sufficient time interval, or alternatively, depositing several drops of a generally concentrated solution of the first biological particles along the substrate surface to completely cover the metallized surface. These first biological particles may be produced in laboratory cultures or obtained from the higher living biological systems as described hereinabove, and are commercially available in highly purified form, and if not available commercially, may be purified chemically. This solution of the first biological particles may typically be a salt solution of water or other liquid appropriate for and not reactive with, the first biological particles. The solution coated substrate 10 is preferably stored in a moist chamber for a time interval sufficient so that the first biological particles in the drops of the solution are adsorbed onto the metallized surface of substrate 10 and form a substantially complete monomolecular layer 11 along the entire top surface of the metallized coating in accordance with the teachings of the aforementioned patent applications. The time interval (generally up to one hour) for the formation of the monomolecular layer 11 on substrate 10 is an inverse function of the concentration of the first particles in solution. A rinsing of the coated surface of substrate 10 is often recommended after the formation of the monomolecular layer 11 thereon. The monomolecular layer coated substrate 10 is then dried, preferably by blowing air at room temperature across substrate in order to speed the drying process. The monomolecular layer 11 has a thickness generally in the range of 30 to 100 A which is, of course, determined by the particular biological particle forming such first layer.

After the monomolecular layer 11 has formed on the metallized surface of substrate 10, a suitable liquid diffusing means is applied to the top surface of the monomolecular layer 11. As illustrated in FIGS. 1a and 1b, a first suitable liquid diffusing means is a cellulose membrane 12 which may be moistened, for example with distilled water, either before or after it is placed on the monomolecular layer coated substrate. Membrane 12 should be placed on the monomolecular layered surface smoothly with sufficient care such that it is in contact with the monolayer metallized surface of substrate 10 along the membranes entire bottom surface. The wet membrane covered substrate assembly is then placed in a moist chamber and a test solution being analyzed for the concentration of the first biological particles is deposited on the wet membrane 12 along a first edge of substrate 10 while a solution containing the second biological particles is deposited along a second edge perpendicular to the first edge. These solutions (of the first and second biological particles) may typically be salt solutions of water or other liquid appropriate to, and not reactive with, such biological particles a blood plasma sample, or a human serum sample. The solutions generally also contain other (nonspecific) biological particles, a typical example of a test solution being human serum, and the other solution rabbit anti-serum. Although such first and second biological particle solutions may be deposited on membrane 12 merely by depositing several drops thereof in relatively closely spaced relationship respectively along the first and second edges of the substrate, a more convenient depositing method is to moisten narrow strips 13 and 14 of a cellulose membrane in the particular solutions, place them on top of the moistened larger cellulose membrane 12 along the two perpendicular edges of substrate 10 and then allow the two solutions to diffuse in membrane 12. Thus, as depicted in FIG. 1a, narrow strips 13 and 14 are respectively oriented parallel to the first and second edges of substrate 10 and equally slightly spaced therefrom. This spacing is not particularly critical and strips 13, 14 could even slightly overlap the respective edges of substrate 10 as in the case of strips illustrated in FIG. 5a. Membrane 12 and strips 13, 14 may be any cellulose or cellulose derivative such as cellulose acetate and can be a porous paper such as any of the common filter papers or simply a tissue paper. The dimensions of membrane 12 are generally slightly larger than that of substrate 10 in order to provide sufficient room along the edges of the substrate for the narrow strips 13 and 14. As a typical example of the dimensions of the various members of the apparatus, for a substrate being a one inch square, membrane 12 may be a 1½ inch square and strips 13 and 14 are each 1¼ inch long and ¼ inch wide. Strips 13, 14 may be as long the adjacent side of substrate 10 or slightly shorter or longer.

Figure 2A:
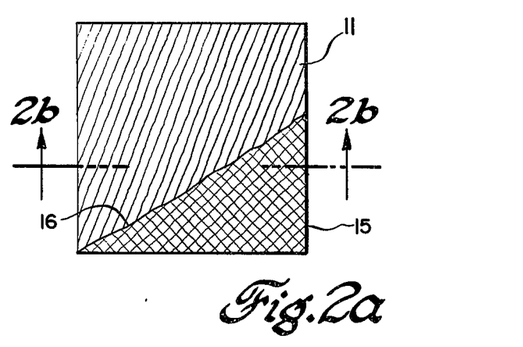
FIG. 2a is a plan view of the metallized solid substrate illustrated in FIG. 1a after the diffusions are completed.
Figure 2B:
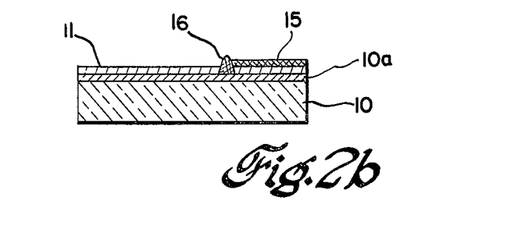
FIG. 2b is an elevation view, in section, of the apparatus illustrated in FIG. 2a taken along line 2b—2b.

During the diffusion of the test and second particle solutions in membrane 12, the first biological particles and other (nonspecific) biological particles in the test solution diffusing from strip 13 permeate through the membrane 12 but do not immunologically react with the monolayer 11 of particles adsorbed on the metallized surface of substrate 10 since both (first) particles are of biological identity. In like manner, the second particle solution diffuses from strip 14 through membrane 12. However, since the second biological particles in the second solution are specific to the first particles of monolayer 11, the second particles immunologically react with the first particles to form a monomolecular layer 15 of the second particles on top of monolayer 11 as illustrated in FIGS. 2a and 2b. The purpose of the diffusing member 12 is thus to hold the moisture therein immobile so that a controlled diffusion of the solutions (and biological particles therein) occurs in the membrane 12 to thereby obtain reproducible results. Along the region of intersection of the two diffusing specimens, there is formed a complexed protein precipitate line 16 several layers thick and results from an immunologic reaction of the diffusing first and second biological particles. Precipitate line 16 is a straight or curved line depending on the types and concentrations of the particles, and the slope thereof is inversely related to the concentration of the first biological particles in the test solution. The time for completion of the diffusions and formation of the precipitate line is a function of the types of first and second biological particles involved, the concentration of each particle in its respective solution, the temperature and the spacing of narrow strips 13 and 14. The time for diffusion of the solutions and formation of the precipitate is generally several hours, although the process can be speeded up to several minutes if electrophoresis is employed.

After formation of the precipitate line 16 on the monolayer metallized surface of substrate 10, the cellulose membrane 12 is peeled from the surface of the substrate leaving the precipitate line 16, adsorbed monolayer 11 region, and double layer region of biological particles 11 and 15 adhered to the metallized surface as shown in FIGS. 2a and 2b. The substrate metallized surface is then rinsed typically with distilled water, and dried preferably by blowing air at room temperature across the substrate. The metallized surface of substrate 10 is then visually examined for the presence of and slope determination of precipitate line 16. Although it has been assumed that the test solution contains the first biological particles in some unkown concentration, this includes the case wherein such test solution is only suspected of containing the first biological particles and in such latter case the absence of a visually detectable precipitate line 16 indicates that the test solution either does not contain any of the first biological particles or contains them in such low concentration that no significant reaction with the second biological particles occurs. The visual examination of the metallized surface of substrate 10 is a direct visual observation in that the unaided eye is employed to observe the light transmitted through the metallized substrate in the case wherein the metallization consists of the indium particles and to observe the reflection off the metallized surface in the case wherein the metallization is the indium-gold alloy and indium oxide film. In the case of the first metallization, the area (of metallized substrate 10) having only the monomolecular layer 11 thereon appears as a first shade of brown, the area containing the double layer 11, 15 is a preceptably still darker shade of brown and precipitate line 16 is a percaptably still darker shade of brown. In the case of the indium-gold alloy, indium oxide film metallization, the precipitate line is a purplish color.

It should be evident that as the concentration of the first biological particles in the test solution applied to narrow strip 13 increases, such particles diffuse to a greater extent than it the concentration was lower and thus the resultant precipitate line 16 has a smaller angle (slope) as measured with reference to the horizontal in FIG. 2a. A quantitative determination of the concentration of the first particles in the test solution can be determined by comparing the slope precipitate line 16 with the slope of a precipitate line on a second substrate wherein a known concentration of the first particles in a "control" solution is applied to a corresponding narrow strip 13.

In the method described hereinabove, it was assumed that the solution applied to strip 14 was a known solution containing the second biological particles. Alternatively, both the first and second solutions may be test solutions suspected of respectively containing the first and second particles in which case formation of the precipitate line indicates that such particles are indeed contained within the respective solutions whereas absence of the precipitate line merely indicates that one or both of the solutions do not contain their respective particles, although in this latter case a monomolecular layer of the nonspecific biological particles in the first and second solution is adsorbed on the substrate metallized surface.

The biological particles referred to hereinabove as first and second biological particles may be antigens, antibodies, viruses, bacteria, hormones, enzymes or other particles which can be readily grown or otherwise isolated and collected, or are present in human serum or other solutions being tested. A typical example of particular biological particles which are detected by the method and the apparatus described hereinabove is hepatitis B antigen (HBAg) as the first biological particles and antibodies to a hepatitis (HBAb) as the second biological particles.

The test for the concentration of particular immunnologically reactive biological particles described hereinabove is known as an indirect test as opposed to the direct test in that presence of the first biological particles in the test solution produces no second monomolecular layer thereof. Thus, in the case of my indirect test for an antigen, and specifically for HBAg, the test solution applied to strip 13 is a human serum sample, a solution containing the antibodies HBAb is applied to strip 14, and a monomolecular layer of the antigen HBAg is initially adsorbed over the entire metallized surface of the substrate. The concentration of the HBAg is then determined from the slope of the precipitate line 16 formed on the substrate wherein the concentration is inversely related to the slope.

The indirect test for determining the presence and concentration of the antibodies such as HBAb is performed oppositely to the indirect test for HBAg with the obvious substitution of a monomolecular layer of the HBAb adsorbed over the entire metallized surface of the substrate, a solution of the HBAg being applied to strip 14 and the test solution applied to strip 13 being a human serum sample taken from a patient suspected of having had hepatitis B. In all of these tests, absence of the first biological particles in the test solution applied to strip 13 results in on precipitate line being formed.

In the above hepatitis tests, the HBAb may be obtained from human serum of a patient known to have had hepatitis B, or it may be developed in a goat, rabbit or other suitable animal by injection thereof with the HBAg, waiting a suitable incubation period such as 2 weeks, and then drawinb drawing drawing the specific antibody from the animal and separating the antibody from the remaining blood particles.

Referring now to FIGS. 3*a* and 3*b*, there is shown a second embodiment of my invention similar to the first embodiment but wherein the moisture holding and specimen diffusing medium is now a thin layer of gel instead of the cellulose membrane. The most common gels suitable for the immunologic reaction tests are agar and agarose. The substrate 10 and metallization 10*a* are of the same type as described with reference to FIGS. 1*a* and 1*b*. The thin layer of gel 30 is formed on top of the monomolecular layer 11 adsorbed onto the metallized surface of substrate 10, and such gel layer is of thickness less than 1 millimeter. The gel solution that is utilized in forming the gel layer may typically be a salt solution, distilled water solution or buffered solution thereof depending upon the biological particle solutions to be utilized in the test. After the gel has solidified, wells 31 and 32 are formed through the thin layer 30 in any convenient manner. Wells 31 and 32 are each of long narrow form similar to the narrow strips 13, 14 in FIG. 1a and oriented in a similar manner with the exception that, since the gel layer does not extend beyond the edges of substrate 10, the perpendicular oriented wells 31 and 32 are within the area defined by the substrate surface and spaced slightly inwardly from the respective edges thereof. The wells 31 and 32 arre generally of equal dimension and have a width as small as one millimeter and as large as 5 millimeters. As illustrated in FIG. 3*a*, the length of wells 31 and 32 is slightly less than the length of the corresponding sides of substrate 10 since the ends of the wells must be contained by the gel. The major distinctions between my invention and the prior art diffusion in gel apparatus as described in the above-referenced book "Methods in Immunology and Immunochemistry" are:

1 My apparatus requires a metallized solid surface since the visible precipitate line resulting from an immunological reaction of biological particles is formed on such monomolecular layer covered metallized surface (although the precipitate line is also formed in the gel). In the prior art apparatus no metallized solid surface is required although a means for merely supporting the gel layer is used.

2. My gel layer is substantially thinner than the prior art gel layer which is at least one mm thickness and is described in the above-referenced book as being in the range of 1–3 mm. This significant change in thickness results from the fact that in my apparatus the gel is utilized merely as a diffusion medium for holding moisture in an immobile state whereas in the prior art apparatus the precipitate line is formed in the gel and therefore requires a thicker layer of gel in order to form a sufficiently thick precipitate line to make it visible.

3. As a result of distinction (2) the precipitate line formed with my invention becomes a durable, and can be a permanent, record of the immunologic reaction and requires no staining to be visible. In the prior art apparatus the gel requires the staining in order for the precipitate line to be visible (with much less contrast than my invention) to the unaided eye.

4. In my invention the wells are formed completely through the gel layer. In the prior art apparatus as noted on page 151 in the above-referenced book, the bottoms of the wells must be sealed from the surface of a plate on which the gel is supported. Although my apparatus operates satisfactorily with the bottom of the wells also being sealed from the monomolecular layer coated metallized surface of substrate 10, such sealing of the bottom of the wells is not necessary, and it is preferred to form the wells completely through the layer of gel as indicated in my FIGURES. This significant distinction between the wells results from the fact that the visible precipitate line in my apparatus is formed on a metallized solid surface whereas in the prior art it is formed within the gel itself.

After the wells 31 and 32 are formed through a gel layer 30, the gel covered, monolayered, metallized solid surface assembly is placed in a moist chamber. Then, the test solution suspected of containing the first immunologically reactive biological particles (and generally other nonspecific particles) corresponding to the biological particles adsorbed onto the metallized surface as monolayer 11, is deposited in well 31. A solution containing the second biological particles (and generally other nonspecific particles) specific to the first particles is deposited into well 32 and the two solutions are allowed to diffuse in the gel in the same manner as with the cellulose acetate membrane in FIG. 1a. Again as in the case of the cellulose membrane, during the diffusion of the two solutions in the gel, the first biological particles in the test solution do not immunologically react with the biologically identical particles in monolayer 11 whereas the second biological particles do react therewith to form a monomolecular layer 15 thereof as shown in FIGS. 2a and 2b. At the intersection of the diffusing first and second particles there is again formed the complexed protein precipitate line 16 show most clearly in FIG. 2 a which again has a slope inversely related to the concentration of the first biological particles in the test solution deposited in well 31. The time for completion of the diffusion and formation of the precipitate line is again a function of the types of biological particles involved, the concentrations thereof, the proximity of wells 31, 32 and the temperature.

After formation of precipitate line 16 on the metallized surface of substrate 10, the layer 30 of gel is peeled or otherwise removed from the metallized solid surface. The metallized surface with the first monolayer 11, second monolayer 15 and precipitate line 16 adhered thereon (as shown in FIG. 2a) is then rinsed with distilled water, dried and then visually examined with the unaided eye to observe the light reflected off, or transmitted through the metallized surface, depending upon the metallization employed as noted hereinabove. The precipitate line 16 is again visible with good contrast to the unaided eye and in both the cellulose membrane and gel embodiments of my invention, a smaller amount of the biological particles is needed to obtain a visually detected precipitate line on the metallized solid surface as compared to the amount of particles needed to form such precipitate line in the cellulose acetate membrane or gel layer in the prior art. Thus, my invention is more sensitive than the prior art in that it results in the determination of concentration of biological particles of much smaller quantity than that obtained with conventional double diffusion in cellulose membrane or gel techniques. Finally, no staining of the precipitate is required, as distinguished from the prior are double diffusion techniques, in order to visually detect the precipitate line, and the contrast is also significantly better than that obtained with the prior art techniques. Again, as in the case of the cellulose membrane embodiment, a quantitative determination of the concentration of the first biological particles in the test solution may be obtained by comparing the slope of the precipitate line with the slope of a precipitate line formed on another metallized substrate wherein a "control" solution (known concentration of first particles) has been deposited into well 31.

Figure 4A:
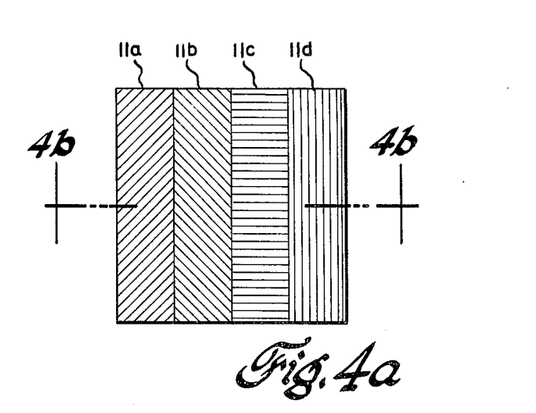
FIG. 4a is a plan view of the metallized solid substrate prior to its being covered with a liquid diffusing medium in third and fourth embodiments of my invention.
Figure 4B:
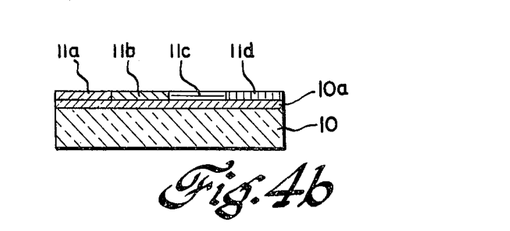
FIG. 4b is an elevation view, in section, of the apparatus illustrated in FIG. 4a taken along line 4b—4b.

Referring now to FIGS. 4a and 4b, there is shown the substrate component of a third (and fourth) embodiment of my invention which is adapted for determining the concentration of a plurality of different biological particles, and as an example, is suitable for determining the concentration of a predetermined number of components in human blood plasma. The metallized substrate is prepared for the test by adsorbing juxtaposed monomolecular layer strips 11a, b, c, d, . . . of the particular plasma components to be investigated on the metallized surface of the substrate. Any number of strips may be utilized as determined by the number of different plasma components to be analyzed. As one example, and not by way of limitation, strips 11a–d of four different plasma component biological particles are adsorbed onto the metallized surface 10a of substrate 10 as shown in FIG. 4a with each strip running the full length of the substrate and the strips preferably being of equal width. Typically, for a 1 inch square substrate, four strips each of 1⁄4 inch width would be adsorbed onto the metallized surface thereof. The particular plasma component biological particles to be analyzed, and therefore adsorbed onto the metallized surface of the substrate would, of course, be determined by the particular medical condition being investigated. As an example, but by no means a limitation, plasma proteins such as albumin, gammaglobulin, heptoglobulin, and plasminogen could be human blood plasma proteins being tested for concentration. Since the four plasma proteins selected generally are not specific to each other, the four strips 11a–d can be arranged with little or no spacing between adjacent strips when adsorbed on the metallized surface 10a of substrate 10. My invention does not preclude the use of two specific biological particles being investigated for concentration in that, if desired, alternate or other spaced apart strips such as 11a and 11c or d etc., could be the heptatitis antigen and antibody, respectively, as a typical example of specific biological particles in a test to determine the concentration of both the antigen and antibody in the patient's blood. This embodiment of my invention for testing multiple components in a test solution such as human blood plasma, as well as the first two embodiments for testing one component, are especially well adapted for the testing of biological particles which generally are in such low concentration that conventional detection methods are either non-existent or not satisfactory due to their low sensitivity.

Figure 5A:
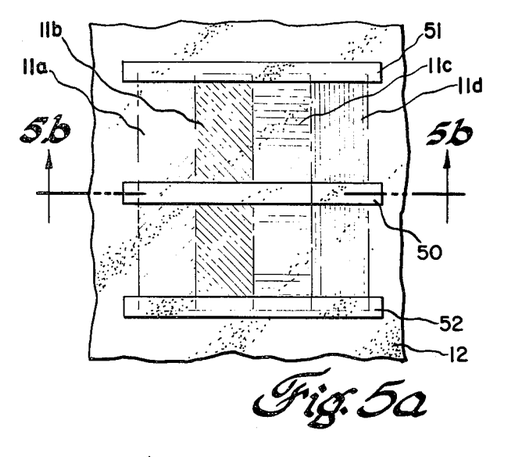
FIG. 5a is a plan view of the third embodiment of my invention prior to the specimens being diffused in a cellulose membrane diffusing member.
Figure 5B:
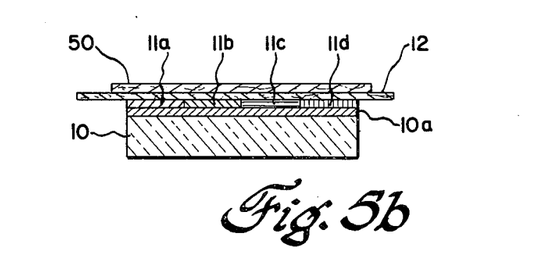
FIG. 5b is an elevation view, in section, of the apparatus illustrated in FIG. 5a taken along line 5b—5b.

After the metallized substrate has been prepared with the plurality of plasma component monolayer strips 11a–d adsorbed thereon, the monolayered substrate is covered with a mioistened cellulose membrane 12 as was done in FIGS. 1a and 1b. An antihuman serum containing antibodies (i.e., biological particles specific to the particles being tested) to the various plasma components in monolayers 11a    d is then applied to the moist membrane 12 along the centerline of substrate 10 in a direction normal to the long dimension of strips 11a–d. The test plasma sample, typically of a patient being routinely examined or suspected of having a disease or other illness which can be diagnosed from the plasma components 11a–d, is applied to the moist membrane 12 along one edge of substrate 10 parallel to the antibody application and a control plasma sample is applied to the moist membrane along the opposite edge. As illustrated in FIGS. 5a and 5b, a convenient means for applying the antibodies, test plasma and control plasma to the moist membrane 12 is to immerse three narrow strips of cellulose membrane in the respective solutions and then placed them on top of the moist membrane 12. Thus, strip 50 along the centerline of substrate 10 is moistened with an antihuman serum containing antibodies to all of the four plasma components forming monolayer strips 11a–d, strip 51 is moistened with a control plasma containing normal concentrations of the four plasma components of strips 11a–d and strip 52 is moistened with the test plasma. Cellulose membrane strips 50, 51 and 52 are each of equal length approximately the length of substrate 10 and are preferably of equal width such as approximately ⅛ inch for a 1 inch square substrate. Strips 51 and 52 are parallel to center strip 50 and are equally spaced therefrom and may overlap the edges of substrate 10, as illustrated, or be slightly spaced therefrom.

The assembly illustrated in FIGS. 5a and 5b is then placed in a moist chamber and the antihuman serum containing antibodies in strip 50 diffuses in membrane 12 outwardly toward strips 51, 52, while at the same time the control plasma diffuses from strip 51 toward strip 50 and the test plasma diffuses from strip 52 toward strip 50. As in the case of the first embodiment of my invention, the first biological particles (control plasma component proteins corresponding to the components of monolayers 11a–d) permeate the membrane 12 but do not immunologically react with the monolayer strip 11a–d biological particles since an immunologic reaction cannot occur between biologically identical proteins. However, the diffusion in membrane 12 of the antibodies in the antihuman serum from center strip 50 toward strip 51 does form four second monomolecular layers 15a, 15b, 15c, 15d of antibodies respectively specific to the plasma component of strips 11a–d since an immunologic reaction does occur between such respective pairs of biological particles.

Figure 6A:
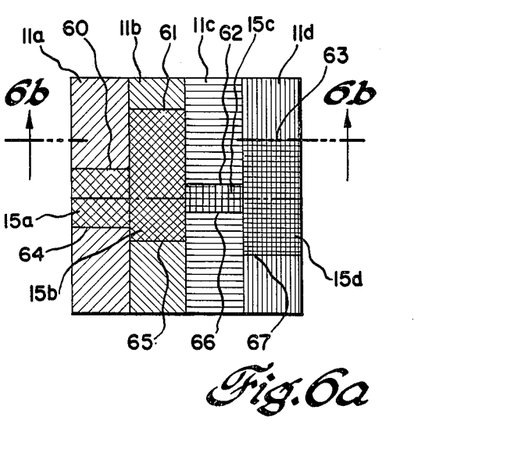
FIG. 6a is a plan view of the metallized substrate in the third and fourth embodiments of my invention after the diffusions are completed.
Figure 6B:
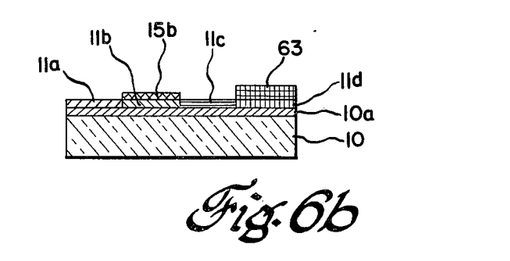
FIG. 6b is an elevation view, in section, of the apparatus illustrated in FIG. 6a taken along line 6b—6b.

As illustrated in FIGS. 6a and 6b, at the intersection of the two diffusing solutions along each strip 11a–d, there is formed a complexed protein precipitate line of several layers thickness which results from an immunologic reaction of each diffusing pair of specific biological particles. Thus, as most clearly illustrated in FIGS. 6a, a first precipitate line 60 is formed across monomolecular layer strip 11a at a distance from the centerline of substrate 10 inversely related to the concentration of the strip 11a blood plasma component in the control plasma sample. In like manner, a second precipitate line 61 is formed across monomolecular layer strip 11b at a distance from the centerline inversely related to the concentration of the strip 11b blood plasma component. In like manner, precipitate lines 62 and 63 are formed across monolayer strips 11c and 11d at distances from the substrate centerline inversely related to the concentrations of the strip 11c and 11d blood plasma components, respectively.

The diffusing antibodies from strip 50 and test sample blood plasma components from strip 52 also result in no formation of a second layer of the blood plasma particles from the test sample along monolayers 11a–d since they are biologically identical proteins. However, the diffusion in membrane 12 of antibodies in the antihuman serum from strip 50 toward strip 52 does form a continuation of the four second monomolecular layers 15a, 15b, 15c, 15d due to the immunological reactions with the particls in the first layers 11a–d. At the intersections of the two diffusing solutions of the antibody and test plasma sample particles along each strip 11a–d, there are formed the preciptiate lines 64, 65, 66 and 67 across strips 11a, 11b, 11c and 11d, respectively, with the distance of each precipitate line from the centerline of the substrate 10 being inversely related to the concentration of the particular blood plasma component in the plasma being tested. The time for completion of the diffusions and formation of the precipitate lines on the metallized substrate in FIGS. 6a and 6b is again a function of the types of biological particles involved, the concentrations thereof, the temperature and the spacing between center strip 50 and strip 51, 52. Thus, the use of a smaller substrate results in the edge strips 51 and 52 being closer to center strip 50 so that the specific particles intersect more rapidly than if a larger substrate with further spaced strips 51 and 52 is employed.

After formation of the various precipitate lines 60–67 on the monolayer strip metallized surface of substrate 10, cellulose membrane 12 is peeled from the substrate surface, the substrate surface with the precipitate lines adhered thereon is rinsed with distilled water, dried and then visually examined with the unaided eye to determine the concentration of the various plasma components in the blood plasma sample being tested. The concentrations are determined by comparing the length of the double layer along each monolayer strip 11a–d from the centerline in the direction of test strip 52 with the length of the double layer along the corresponding monolayer strip from the centerline in the direction of control strip 51. Another way of determining this concentration is by measuring the distances of the two precipitate lines on each component strip from the opposite substrate edges. An equal length of the double layer on a particular component strip, (i.e., equal distance of precipitate lines from the substrate edges) indicates that the component in the test plasma is equal to the normal concentration thereof in the control sample. This can be seen to exist for the plasma components in strips 11a, 11c and 11d. However, on strip 11b it is noted that the second layer 15b extends toward the lower (test sample) edge of substrate 10 as depicted in FIG. 6a a smaller distance from the centerline than it does toward the upper (control) edge, that is, precipitate line 65 is spaced further from the lower edge than is precipitate line 61 from the upper edge. This difference indicates that the concentration of the plasma component of monolayer 11b in the test sample is of higher concentration than normal as indicated by the control sample. Thus, a quick visual observation with the unaided eye of the coated substrate immediately indicates whether the plurality of plasma components being tested have normal or abnormal concentrations. As in the case of the first two embodiments, the visual observation may be by reflected light off the metallized surface or by viewing the transmitted light through the substrate depending upon the metallization utilized on the substrate.

Figure 3A:
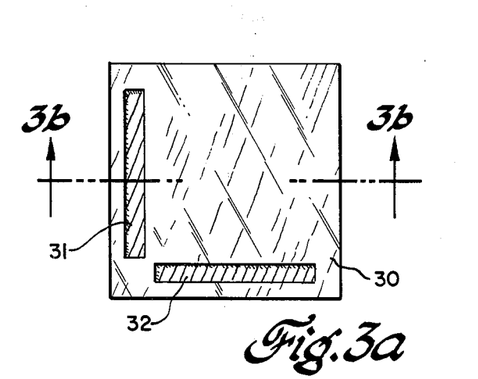
FIG. 3a is a plan view of a second embodiment of my invention similar to the first embodiment but utilizing a thin layer of gel as the diffusing medium.
Figure 3B:
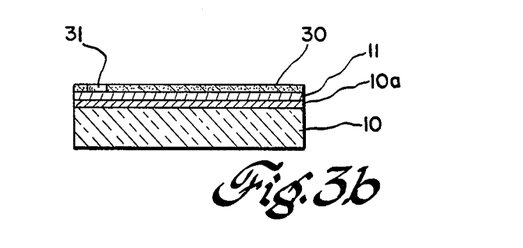
FIG. 3b is an elevation view, in section, of the apparatus illustrated in FIG. 3a taken along line 3b—3b.
Figure 7A:
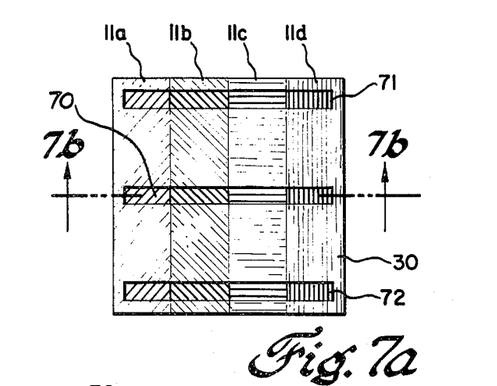
FIG. 7a is a plan view of the fourth embodiment of my invention similar to the third embodiment but utilizing a thin layer of the gel as the diffusing medium.
Figure 7B:
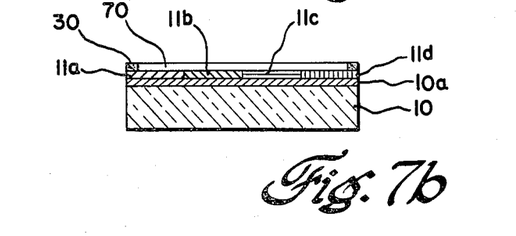
FIG. 7b is an elevations view, in section, of the apparatus illustrated in FIG. 7a taken along line 7b—7b.

Referring now to FIGS. 7a and 7b, there is shown a fourth embodiment of my invention which is related to the third embodiment of FIG. 5a, 5b in the same manner as the second embodiment to the first. That is, a thin layer of gel 30 is utilized in place of cellulose membrane 12 for holding moisture immobile and functioning as a diffusion medium. Thus, corresponding to the FIGS. 5a and 5b embodiment, central well 70 and parallel wells 71 and 72 along opposite edges of substrate 10 provide the means for depositing the antibodies, control sample and test sample to the diffusing means. As in the case of the FIGS. 3a and 3b embodiment, wells 70, 71 and 72 are slightly shorter than the length of substrate 10, of width between 1 and 5 millimeters and are formed completely through the thin gel layer which is of thickness less than 1 millimeter. Wells 71 and 72 are equally spaced from well 170 and all three wells are oriented perpendicular to monomolecular layer strips 11a, 11b, 11c and 11d. Substrate 10 can be of the same size as in the FIGS. 5a and 5b embodiment. After the antibody, control and test samples have been deposited into respective wells 70, 71 and 72, they diffuse through the gel sufficient to form the second monolayers 15a, 15b, 15c, 15d and precipitate lines 60–67 as shown in FIGS. 6a and 6b. The thin gel layer 30 is then removed, the metallized surface of substrate 10 is rinsed with distilled water, dried and then visually examined in the same manner as with my third embodiment. That is, the lengths of the double layers along the monolayer strips 11a–d from the centerline toward the upper and lower edges of substrate 10 as seen in FIG. 6a are compared, or the distances of the precipitate lines from such substrate edges are compared to quickly indicate whether the various components of the test sample are of normal or abnormal concentration.

In the embodiments of my invention described hereinabove, it is noted that no staining of the cellulose membrane or gel is required in order to make visible and permanent the precipitate line(s) and thus a complex step in the prior art technique is eliminated with my apparatus. That is, in the prior art Ouchterlony technique of double diffusion in gel, the nonspecific particles are first removed in a water bath requiring approximately 24 hours, then staining the gel, another washing process to remove the stain in the gel material, but not from the precipitate line, and finally drying the gel in a slow delicate process. Also, the greater sensitivity of my apparatus, in that the plurality of layers of biological particles which form the precipitate line, as well as the double monolayers, are more easily detectable, makes my testing method more sensitive than the prior art techniques. That is, the precipitate line is more readily visible (for the same amount of biological particles) on the metallized substrate than in the cellulose membrane or gel, and therefore a smaller amount of such particles can be detected with my appparatus. Since my apparatus is more sensitive than the prior art apparatus, a lesser amount of the first biological particles and smaller specimens of the test solution may be deposited on the cellulose membrane or into the wells of the gel layer in my apparatus and therefore an economy in the use of such particles is realized which may be particularly significant in the case where the first particles are obtained from a costly laboratory process, and, or, where the physical condition of the patient is so poor that the taking of a large sample from him may be detrimental to his medical condition.

From the foregoing description, it can be appreciated that my invention makes available an improved surface indirect test method and apparatus for determining the concentration of biological particles in a test solution by direct visual observation of the metallized surface of a solid substrate on which a secod monolayer ad complexed protein precipitate is formed as a result of an immunological reaction between first biological particles being investigated and second biological particles specific to the first particles wherein such reaction occurs on top of a first monolayer of the first particles absorbed on the metallized surface of the substrate. My method and apparatus are very simple in that only a moistened cellulose membrane or thin layer of gel with suitable wells formed therethrough is required on the monolayer absorbed metallized surface of the substrate member for diffusion of the solutions and the unique and highly sensitive properties of the metallized substrate member thereby avoids the need for staining the cellulose membrane, gel or substrate in order to detect the precipitate line by direct visual observation. As a result, I have provided a simple method wherein the previously described metallized slide described in the hereinabove-referenced patent applications can now be adapted for use with diffusions of various solutions in a cellulose membrane or thin gel layer for determining the concentration of particular biological particles. Since the metallized slides can be fabricated repetitively with identical characteristics, the results of the quantitative surface indirect test in accordance with my present invention are very consistent and can serve many useful purposes, especially in the medical diagnostic field in the analysis of human serum, for example, for the determination of the various antibodies and antigens therein and particularly those of low concentration for which prior art methods are either nonexistent or not satisfactory. Since the visual contrast between the precipitate line and monolayer of biological particles is very distinct when utilizing my metallized solid substrate, the concentration determination is accomplished by direct observation with the unaided eye and therefore does not require elaborate test equipment and obtains the precipitate line in durable form.

Having described my invention with reference to four specific embodiments, it is believed obvious that modification and variation of my invention is possible in the light of the above teachings. Thus, the shape and size of the solid substrate member and cellulose membrane or thin layer of gel may be varied and virtually any pair of immunologically reactive biological particles which will immunologically react with each other can have the concentration of one of them being detected with my apparatus. Further, metallizations other than the indium, indium-gold and indium-gold alloy and indium oxide may be found to obtain better contrast of the precipitate line and double layers on the metallized surface for some specific biological particles. Also, the irregular surface embodiment of my metallized slide could obviously be fabricated by starting with an irregular surface substrate and evaporating constant thickness layers of a metal such as indium thereon. Finally, it should be evident that first and second embodiments of my apparatus may also be utilized for determining the concentration of biological particles by the direct method wherein no monomolecular layer of first biological particles is adsorbed along the entire metallized surface of the solid substrate. Thus, in the first and second embodiments of my invention a monomolecular layer of the first biological particles would be adsorbed directly onto a portion of the metallized surface of the substrate extending from the left edge as most clearly illustrated in FIG. 2a whereas a monomolecular layer of the second biological particles would be absorbed directly onto the metallized surface of the substrate on portion extending from the bottom edge of the substrate and the intersecting first and second particles form a precipitate line 16 whose slope would again be inversely related to the concentration of the first particles in their solution. The slopes of the precipitate lines for the same concentration of particles in the inhibition test and direct tests may not necessarily be identical since the time for the second particles to adsorb onto the metallized surface of the substrate may not be identical with the time to immunologically react with the first particles in the inhibition test method. Thus, the first and second embodiments of my apparatus as fabricated may consist of a metallized substrate with or without a monomolecular layer of first immunologically reactive biological particles adsorbed thereon and with either a cellulose membrane or thin layer of gel with perpendicular oriented specimen depositing means thereon. It is, therefore, to be understood that changes may be made in the particular embodiments of my invention as described which are within the full intended scope of the invention as defined by the following claims.

What I claim as new and desire to secure by Letters Patent of the U.S. is:

1. Apparatus for determining the concentration of immunologically reactive biological particles in a test solution, comprising in combination:
   a solid substrate member having a metallized major surface,
   a layer of first immunologically reactive biological particles adsorbed over at least a portion of said metallized surface,
   means in substantially complete contact with the outer surface of said layer of first biological particles for holding a quantity of moisture in the immobile state whereby the moisture can function as a diffusing medium,
   means for placing a first straight longitudinally-extending deposit of solution into contact with said moisture along the length of said first deposit, and
   means for placing a second straight longitudinally-extending deposit of solution into contact with said moisture along the length of said second deposit, said first and second deposits extending in a particular orientation relative to each other whereby the solutions of said first and second depposits will diffuse through said moisture toward each other and toward said layer of first biological particles.

2. The apparatus set forth in claim 1 wherein said solid substrate member is formed of a light-transmissive material selected from the group consisting of glass and plastic.

3. The apparatus set forth in claim 1 wherein said solid substrate member is formed of metal.

4. The apparatus set forth in claim 1 wherein the metallized surface of said solid substrate member is a metal and an oxide film thereof.

5. The apparatus set forth in claim 1 wherein the major surface of said solid substrate member is flat.

6. The apparatus set forth in claim 1 wherein the first and second deposits extend in directions perpendicular to each other.

7. The apparatus set forth in claim 1 wherein the metallized surface of said solid substrate member is a noncontinuous film consisting of metal particles.

8. The apparatus set forth in claim 7 wherein the noncontinuout film consists of indium particles.

9. The apparatus set forth in claim 1 wherein the metallized surface of said solid substrate member is formed from an alloy of two metals.

10. The apparatus set forth in claim 9 wherein the alloy of two metals is an alloy of indium and gold.

11. The apparatus set forth in claim 1 wherein the metallized surface of said substrate member is formed from an alloy of two metals and has an outer oxide film of one of the two metals.

12. The apparatus set forth in claim 11 wherein the two metals are indium and gold and the oxide film is an indium oxide film.

13. The apparatus set forth in claim 1 wherein said holding means is a moistened cellulose membrane.

14. The apparatus set forth in claim 13 wherein said cellulose membrane is moistened with distilled water and is of size sufficient so that the edges thereof overlap the edges of the solid substrate member.

15. The apparatus set forth in claim 1 wherein said holding means is a thin layer of gel.

16. The apparatus set forth in claim 15 wherein the means for placing first and second deposits of solution are long and narrow wells formed through the layer of gel and extend in directions in perpendicular to each other.

17. The apparatus set forth in claim 15 wherein the gel layer thickness is less than one millimeter.

18. The apparatus set forth in claim 15 wherein said thin layer of gel extends over substantially the entire outer surface of said first monomolecular layer of first biological particles, and the gel material is agar.

19. The apparatus set forth in claim 1 wherein the means for placing the first and second deposits are disposed parallel to and spaced from each other and parallel to and spaced from means for placing a third straight longitudinally-extending deposit of solution into contact with the moisture along the length of said third deposit.

20. The apparatus set forth in claim 19 wherein the holding means is a cellulose membrane and each means for placing a deposit is a strip of cellulose membrane disposed on the outer surface of the holding means.

21. The apparatus set forth in claim 19 wherein a plurality of layers of different immunologically reactive biological particles are employed, each layer being disposed over a separate portion of the metallized surface and being adsorbed directly thereon, the plurality of layers being arranged as a series of strips extending perpendicular to the several means for placing deposits of solution.

22. The apparatus set forth in claim 21 wherein the biological particles of each strip represents a different component of human blood plasma.

23. A method for determining the concentration of immunologically reactive biological particles in a test solution comprising the steps of:

depositing a layer of first biological particles on a metallized surface, disposing a quantity of moisture in the immobile state over and in contact with the outer surface of said layer, placing a straight longitudinally-extending deposit of test solution suspected of containing first biological particles into contact with said moisture along the length of said test solution deposit, placing a straight longitudinally-extending deposit of second solution containing biological particles specific to said first biological particles into contact with said moisture along the length of said second solution deposit, said test solution and second solution deposits extending in a particular orientation relative to each other whereby the solutions will diffuse through said moisture toward each other and toward said layer of biological particles, preventing loss of moisture during the diffusion of said test and second solutions, removing said immobilized moisture and inspecting the exposed surface to determine the location of any complexed precipitate line that may have formed and its relationship to the placement of either or both of said test solution and second solution deposits, and relating the location of the precipitate line, if formed, to the concentration of the immunololgically reactive particles in the test solution.

24. The method set forth in claim 23 wherein the step of examining the metallized surface consists of observing the light reflected off the metallized surface.

25. The method set forth in claim 23 wherein the step of examining the metallized surface consists of observing the light transmitted through the metallizied surface.

26. The method set forth in claim 23 wherein the test solution deposit and the second solution deposit are arranged in an orientation in which they extend in directions perpendicular to each other, whereby any complexed precipitate line generated will be angularly disposed relative to said deposits.

27. The method set forth in claim 23 wherein the disposing of a quantity of moisture in the immobile state is accomplished by depositing a water-moistened porous membrane over and in contact with the outer surface of the layer of first biological particles, the placing of the test solution deposit is accomplished by the use of a first long narrow strip of porous membrane moistened in the test solution and then disposed on the surface of the water-moistened membrane, the step of placing the second solution deposit being accomplished by the use of a second long narrow strip porous membrane moistened in the second solution and then disposed on the surface of the water-moistened membrane extending in a direction perpendicular to said first strip, said water-moistened membrane and first and second strips each being of a material selected from the group consisting of cellulose and cellulose derivatives.

28. The method set forth in claim 23 wherein the step of disposing moisture in the immobile state is accomplished by the use of a thin layer of gel and the depositions of test solution and second solution are made in long narrow wells extending through said gel layer.

29. The method set forth in claim 23 wherein in depositing the layer of first biological particles a plurality of layers are deposited, each layer being of a different immunologically reactive biological particle and being adsorbed directly on a separate portion of the metallized surface, the test solution and second solution deposits being disposed parallel to and spaced from each other and also disposed parallel to, spaced from and on opposite sides of a third straight longitudinally-extending deposit of a control solution, sasid third deposit being placed into contact with the moisture along the length of said third deposit, the plurality of layers being arranged as a series of strips extending generally perpendicular to the several deposits of solution and the step of inspecting the exposed surface includes a comparison between the distance of the test solution precipitate line from said third deposit with the distance of the second solution precipitate line from said third deposit for the same strip.

30. The method set forth in claim 29 wherein the biological particles of each strip represents a different component of human blood plasma.

31. A method for determining the concentration of immunologically reactive biological particles in a test solution comprising the steps of:

disposing a quantity of moisture in the immobile state over and in contact with the outer surface of said layer, placing a straight longitudinally-extending deposit of test solution suspected of containing first biological particles into contact with said moisture along the length of said test solution deposit, placing a straight longitudinally-extending deposit of second solution containing biological particles specific to said first biological particles into contact with said moisture along the length of said second solution deposit, said test solution and second solution deposits extending in a particular orientation relative to each other whereby the solutions will diffuse through said moisture toward each other and toward said layer of biological particles, preventing loss of moisture during the diffusion of said test and second solutions, removing said immobilized moisture and inspecting the exposed surface to determine the location of any complexed precipitate line that may have formed and its relationship to the placement of either or both of said test solution and second solution deposits, and relating the location of the precipitate line, if formed, to the concentration of the immunologically reactive particles in the test solution.

32. The method set forth in claim 31 wherein the metallized surface employed consists of a metal and an oxide film thereof.

33. The method set forth in claim 31 wherein the test solution and second solution deposits extend in directions perpendicular to each other.

34. The method set forth in claim 31 wherein in depositing the layer of first biological particles a plurality of layers are deposited, each layer being of a different immunologically reactive biological particle and being adsorbed directly on a separate portion of the metallized surface, the test solution and second solution deposits being disposed parallel to and spaced from each other and also disposed parallel to, spaced from and on opposite sides of a third straight longitudinally-extending deposit of a control solution, said third deposit being placed into contact with the moisture along the length of said third deposit.

the plurality of layers being arranged as a series of strips extending perpendicular to the several deposits of solution and the step of inspecting the exposed surface includes a comparison between the distance of the test solution precipitate line from said third deposit with the distance of the second solution precipitate line from said third deposit for the same strip.

35. The method set forth in claim 31 wherein the metallized surface employed is a non-continuous film consisting of metal particles.

36. The method set forth in claim 35 wherein the non-continuous film consists of indium particles.

37. The method set forth in claim 31 wherein the metallized surface employed is formed from an alloy of two metals.

38. The method set forth in claim 37 wherein the alloy of two metals is an alloy of indium and gold.

39. The method set forth in claim 31 wherein the metallized surface employed is formed of an alloy of two metals with the surface thereof containing oxide of one of the two metals.

40. The method set forth in claim 39 wherein two metals are indium and gold and the oxide is indium oxide.

* * * * *